(12) United States Patent
Reck et al.

(10) Patent No.: US 9,574,956 B2
(45) Date of Patent: Feb. 21, 2017

(54) MEMS OPTICAL SENSOR

(71) Applicant: Technical University of Denmark, Kgs. Lyngby (DK)

(72) Inventors: Kasper Reck, Herringløse (DK); Christian Østergaard, København N (DK); Ole Hansen, Høsholm (DK); Erik Vilain Thomsen, Lynge (DK)

(73) Assignee: Technical University of Denmark (DK)

( * ) Notice: Subject to any disclaimer, the term of this patent is extended or adjusted under 35 U.S.C. 154(b) by 116 days.

(21) Appl. No.: 14/405,938

(22) PCT Filed: Jun. 6, 2013

(86) PCT No.: PCT/EP2013/061701
§ 371 (c)(1),
(2) Date: Dec. 5, 2014

(87) PCT Pub. No.: WO2013/182643
PCT Pub. Date: Dec. 12, 2013

(65) Prior Publication Data
US 2015/0131100 A1 May 14, 2015

Related U.S. Application Data

(60) Provisional application No. 61/656,051, filed on Jun. 6, 2012.

(30) Foreign Application Priority Data

Jun. 6, 2012 (EP) .................................. 12171002

(51) Int. Cl.
*G01L 1/24* (2006.01)
*G01L 11/02* (2006.01)
*G01N 21/55* (2014.01)
*G02B 6/10* (2006.01)

(52) U.S. Cl.
CPC ................ *G01L 1/246* (2013.01); *G01L 11/02* (2013.01); *G01N 21/55* (2013.01); *G02B 6/10* (2013.01);
(Continued)

(58) Field of Classification Search
CPC ................... G01N 21/7703; G01N 2021/7773; G01N 21/774; G01N 2021/7779; G01N 21/55; G01N 21/65; G01N 2201/061; G01N 2201/0633; G01N 2201/084; G01B 11/18; G01B 2290/25; G01J 3/0218; G01J 3/02
See application file for complete search history.

(56) References Cited

U.S. PATENT DOCUMENTS

2008/0095495 A1* 4/2008 Taverner ................ G01K 11/00
385/30

FOREIGN PATENT DOCUMENTS

GB     2 332 272 A     6/1999

OTHER PUBLICATIONS

International Searching Authority, International Search Report—International Application No. PCT/EP2013/061701, dated Nov. 15, 2013, together with the Written Opinion of the International Searching Authority, 13 pages.

(Continued)

*Primary Examiner* — Michael P Stafira
(74) *Attorney, Agent, or Firm* — Sunstein Kann Murphy & Timbers LLP

(57) ABSTRACT

The present invention relates to an all-optical sensor utilizing effective index modulation of a waveguide and detection of a wavelength shift of reflected light and a force sensing system accommodating said optical sensor. One embodiment of the invention relates to a sensor system comprising at least one multimode light source, one or more optical sensors comprising a multimode sensor optical waveguide accommodating a distributed Bragg reflector, at least one transmitting optical waveguide for guiding light from said at least one light source to said one or more multimode sensor optical waveguides, a detector for measuring light reflected (Continued)

from said Bragg reflector in said one or more multimode sensor optical waveguides, and a data processor adapted for analyzing variations in the Bragg wavelength of at least one higher order mode of the reflected light.

18 Claims, 13 Drawing Sheets

(52) U.S. Cl.
CPC .................. *G01N 2201/061* (2013.01); *G01N 2201/0633* (2013.01); *G01N 2201/084* (2013.01)

(56) References Cited

OTHER PUBLICATIONS la Cour, et al., "Design and Fabrication of Hollow Core MEMS Optical Microphone", M.Sc. Thesis Aug. 8, 2011.
Østergaard, "MEMS Optical Strain Sensors Based on Hollow Core Waveguides with Integrated Bragg Gratings", M.Sc. Thesis, Feb. 2011.
Reck, et al., "Hollow core MOEMS Bragg grating microphone for distributed and remote sensing", 16$^{th}$ Int. Solid-State Sensors, Actuators and Microsystems Conference (Transducers 2011) : Beijing, CH, pp. 586-589, Jun. 5, 2011.
Reck, "MEMS Optical Sensor Systems", Ph.d. Thesis, 2011.
Sang, et al., "Bragg gratings in multimode optical fibres and their applications", Journal of Optoelectronics and Advanced Materials, vol. 8, No. 4, pp. 1616-1621, Aug. 2006.
Wanser, et al., "Novel fiber devices and sensors based on multimode fiber bragg gratings", Proc. SPIE 2360, Tenth International Conference on Optical Fibre Sensors, 265, dated Sep. 14, 1994.
Chinese Patent Office, In Chinese: Office Action dated Oct. 17, 2016 pertaining to Chinese Application No. 201380030307.X, 8 pages.
Chinese Patent Office, English Translation: Office Action dated Oct. 17, 2016 pertaining to Chinese Application No. 201380030307.X, 13 pages.
Zhao, et al., "Hollow waveguides with low intrinsic photoluminescence fabricated with $Ta_2O_5$ and $SiO_2$ films," American Institute of Physics, Applied Physics Letters, vol. 98, 4 pages, Mar. 2, 2011.

* cited by examiner

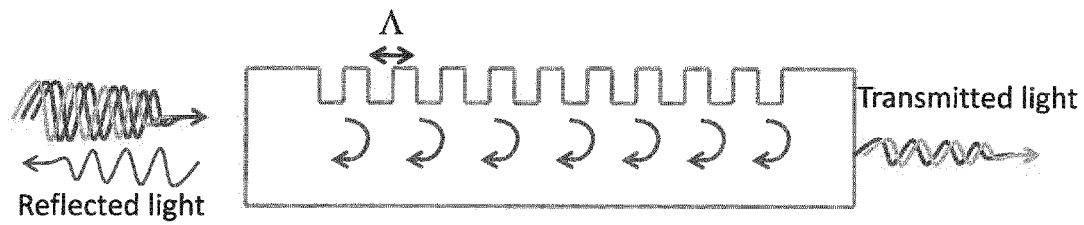
Fig. 1a
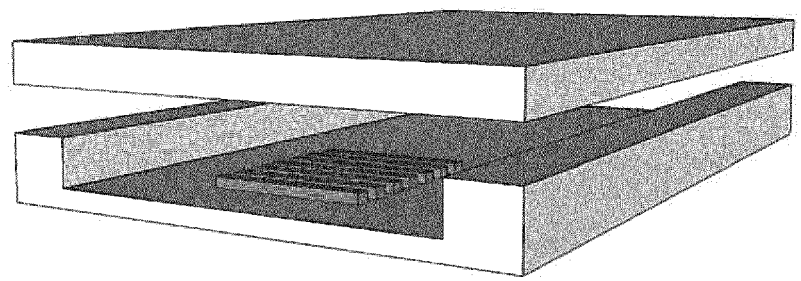
Fig. 1b
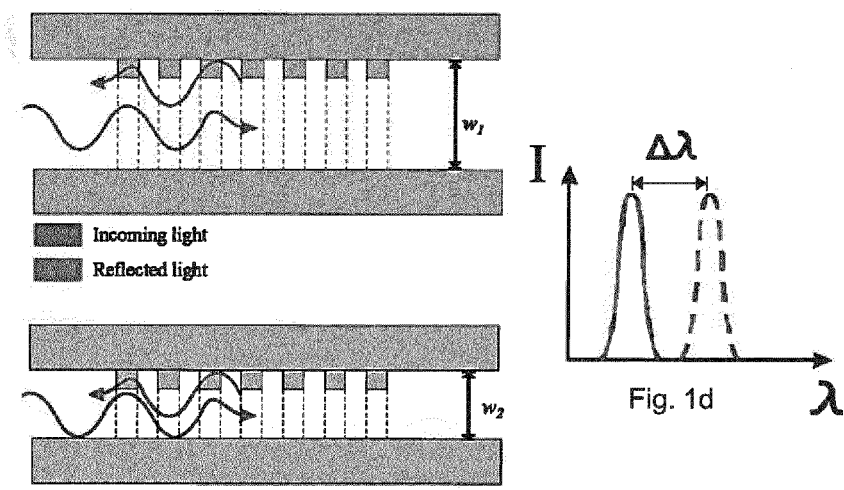
Fig. 1c
Fig. 1d

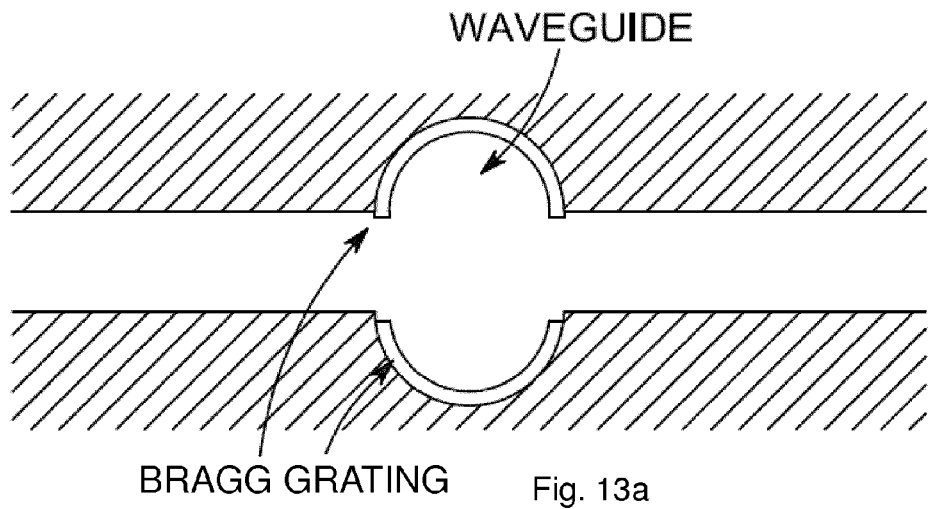
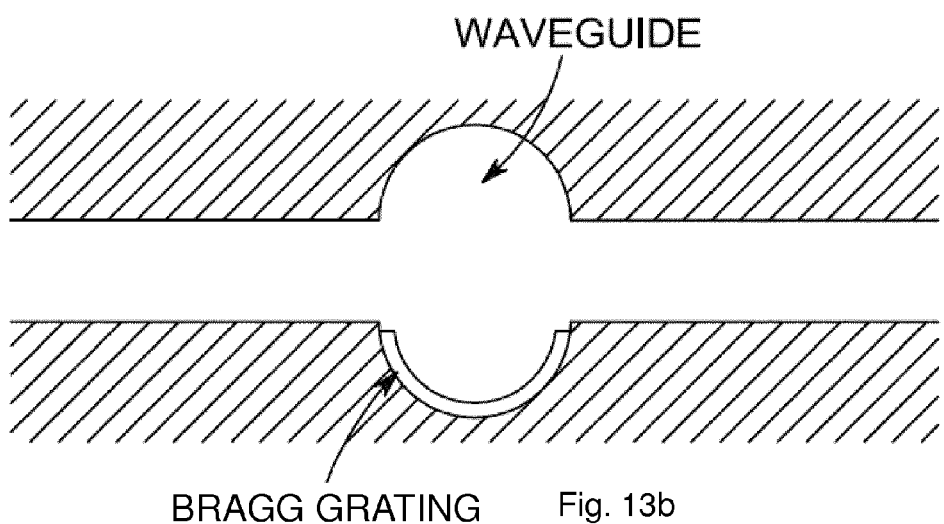

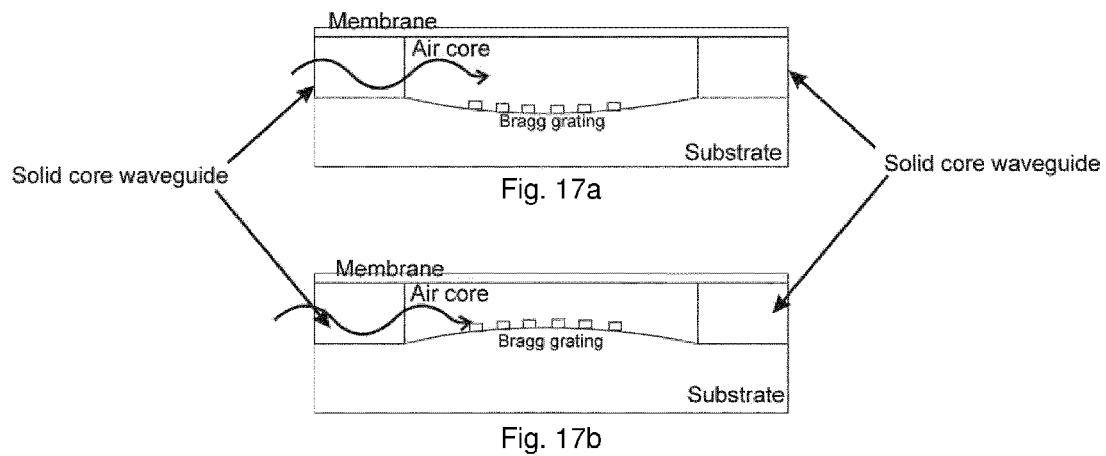
Fig. 17a
Fig. 17b
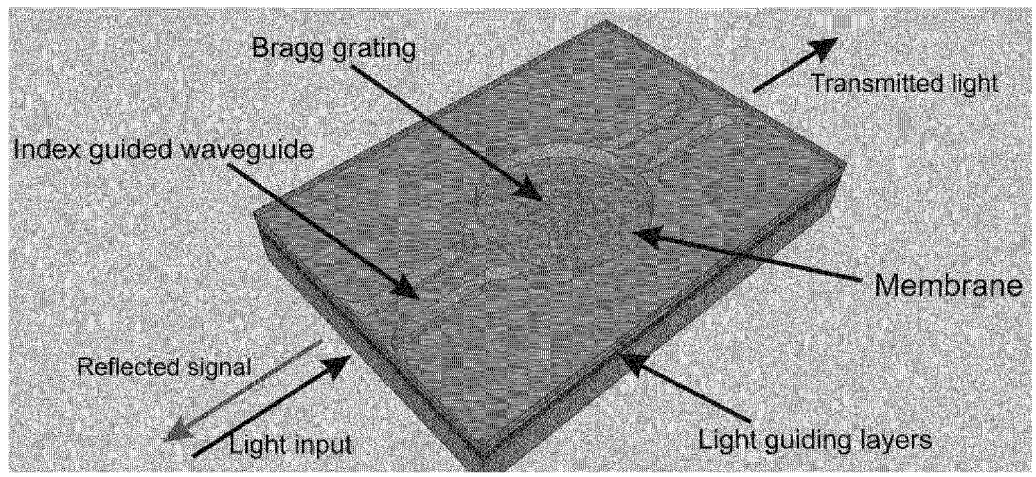
Fig. 18 ptical Sensor," and this application claims priority to U.S.
MEMS OPTICAL SENSOR

CROSS REFERENCE TO RELATED APPLICATIONS

This application is a 35 U.S.C. §371 U.S. national phase of PCT/EP2013/061701, filed Jun. 6, 2013, titled "MEMS Optical Sensor," and this application claims priority to U.S. Provisional Patent Application No. 61/656,051, filed Jun. 6, 2012, and European Patent Application No. 12171002.4, filed Jun. 6, 2012, the entire contents of each of which are hereby incorporated by reference herein, for all purposes.

The present invention relates to an all-optical sensor utilizing effective index modulation of a waveguide and detection of a wavelength shift of reflected light and a force sensing system accommodating said optical sensor.

BACKGROUND OF INVENTION

A sensor is a device that detects a specific physical quantity belonging to the sensor environment, through the means of one or more detection mechanisms which converts the physical quantity to a sensor specific output signal. Well known examples of often used sensors include thermometers, speedometers, microphones, voltmeters, radars and seismometers. A subset of the general sensor concept is the mechanical sensors which detects a property of classical mechanics, e.g. acceleration, pressure and strain, and should be distinguished from sensors used for e.g. biological, medical and chemical sensing. The vast majority of modern mechanical sensors are made using microelectromechanical system (MEMS) technology, as MEMS allows for small scale sensors and inexpensive mass production. With the development of MEMS technology and the advent of micro optical sensing technologies the expanded term microoptoelectromechanical systems (MOEMS) has become widely accepted. MOEMS allows for much more versatile sensor designs and detection of quantities in more difficult accessible environments than previous technologies.

All-optical sensors have a number of advantages that make them interesting for a broader range of applications, such as the low transmission loss in optical fibers which enables remote sensing. However, compared to the vast number of electrical and opto-electrical sensors available today, all-optical sensors currently represent a small niche, since most all-optical sensors cannot in general compete with their electrical counterparts when it comes to sensitivity, dynamic range or price.

The dominating all-optical frequency modulated (FM)-based sensor today is the fiber Bragg grating (FBG) sensor where the deformation of a Bragg grating is used for modulating the signal. While FBGs have successfully been used for a number of applications they have several drawbacks, including the large physical size, low sensitivity, strict limitations on materials choice and component structuring as well as mass production shortcomings. The inventors have previously presented a novel highly sensitive all-optical pressure sensor for an audio microphone fabricated using MEMS technology. The sensing mechanism is based on modifying the effective refractive index of a hollow core anti-resonant reflecting optical waveguide (ARROW) incorporating a Bragg grating. By modifying the effective refractive index instead of the grating period a highly improved sensitivity is obtained. Sensitivities can be up to several magnitudes larger than in FBGs and comparable MEMS technology.

SUMMARY OF INVENTION

In order to obtain the desired sensitivity of the pressure sensor for the audio microphone the inventors developed a highly sophisticated waveguide design. However, even with MEMS technology these waveguide designs turned out to be difficult to realise in practise and consistently low coupling losses could not be obtained. To realize the potential of all-optical sensors other waveguide designs might therefore be necessary. However, the inventors have discovered a new way of greatly improving the sensitivity of all-optical sensors. Presently it is preferred that only the fundamental mode of the light is propagating in the waveguide and thus only reflections from the fundamental mode are analysed. In the scientific community higher order modes are considered undesirable as they are more difficult to control.

But the present inventors have realized that higher order modes are indeed desirable for sensing applications. In general higher order modes have a higher spatial variation than lower order modes. In multimode waveguides incorporating a Bragg grating, several distinct peaks will be reflected from the grating due to the reflection of each mode and the coupling between the modes. Since the individual mode shapes differ in their spatial distribution, their overlap with the grating will in general differ. The difference in mode-grating overlap for the different modes is seen in the change in Bragg wavelength of the individual modes as the waveguide dimensions are changed, i.e. the wavelength sensitivity to waveguide dimensions are mode dependent. Having realized that higher orders modes are preferred for sensing applications, the inventors further discovered that high sensitivity can be obtained with just simple waveguide designs. A first aspect of the invention therefore relates to an optical sensor for a force sensing system comprising a waveguide accommodating a non-solid core for confining light, at least one distributed Bragg reflector, and at least one deflecting element adapted for changing the geometry and/or dimension of the waveguide when submitted to a force, e.g. a force due to acceleration, pressure, displacement, strain, etc. As sensing may be based on higher order mode propagation and reflection, e.g. using light form a multimode light source, the waveguide may have a simple planar or strip geometry thereby greatly distinguishing this optical sensor from the known more complicated designs.

A change in the geometry and/or dimension of the core is in most cases a consequence of a change in the geometry and/or dimension of the waveguide. E.g. the deflecting element forms part of the waveguide and when the deflecting element moves the geometry and/or dimension of the waveguide is changed. Thus, change in geometry and/or dimension of waveguide or core may be used interchangeably herein. The waveguides mentioned herein comprises one or more cores, typically one core. The confinement of light in a waveguide is typically provided in the core, thus propagation of light in a waveguide implicitly means that the light propagates in the core. Thus propagation of light in waveguide and core is used interchangeably herein. Furthermore, as implicit herein at least one of said at least one distributed Bragg reflectors is preferably at least partly located in the non-solid core of the waveguide.

A further embodiment is directed to the use of this optical sensor in a force sensing system. A yet a further embodiment is directed to a force sensing system comprising the above mentioned optical sensor.

A further embodiment of the invention makes use of the new possibilities of higher order mode based sensing by disclosing a sensor system comprising at least one light source, one or more optical sensors comprising a sensor optical waveguide accommodating a distributed Bragg reflector, said sensor optical waveguide adapted for guiding at least one higher order mode of the light from said at least one light source, at least one transmitting optical waveguide for guiding light from said at least one light source to said one or more sensor optical waveguides, a detector for measuring light reflected from said Bragg reflector in said one or more sensor optical waveguides, and a data processor adapted for analysing variations in the Bragg wavelength of said at least one higher order mode of the reflected light.

Correspondingly the present invention also relates to sensor system comprising at least one light source, one or more optical sensors comprising a multimode sensor optical waveguide accommodating a distributed Bragg reflector, at least one transmitting optical waveguide for guiding light from said at least one light source to said one or more sensor optical waveguides, a detector for measuring light reflected from said Bragg reflector in said one or more multimode sensor optical waveguides, and a data processor adapted for analysing variations in the Bragg wavelength of at least one higher order mode of the reflected light.

Knowing that higher order mode based sensing is the way towards better sensitivity the present inventive discovery may also be utilized for improving presently known optical sensors that are capable of guiding at least one higher order mode. A further embodiment of the invention therefore relates to a method for improving the sensitivity of a sensor system comprising at least one sensor optical waveguide suitable for guiding at least one higher order mode of light, said method comprising the step of analysing a plurality of reflected signals from the optical sensor system for detecting a change in Bragg wavelengths of said at least one higher order mode of the reflected light. Correspondingly one embodiment relates to a method for improving the sensitivity of a sensor system comprising at least one multimode sensor optical waveguide wherein multimoded light is propagating, said method comprising the step of analysing a plurality of reflected signals from the optical sensor system for detecting a change in Bragg wavelengths of said at least one higher order mode of the reflected multimoded light.

The inventors have previously presented detailed work on optical sensors based on hollow core waveguides. These publications include Kasper Reck: "MEMS Optical Sensor Systems", Ph.d. Thesis (2011) Christian Østergaard: "MEMS Optical Strain Sensors Based on Hollow Core Waveguides with Integrated Bragg Gratings", M.Sc Thesis (2011). Mette Funding la Cour and Søren Vang Fischer: "Design and Fabrication of Hollow Core MEMS Optical Microphone", M.Sc. Thesis (2011)

Details on the background theory, design and manufacturing details of optical sensor waveguides can be found in these publications, which are therefore incorporated by reference in their entirety.

One embodiment of the present invention is a sensor based on the concept of effective index modulation due to a change in geometry of the waveguide. This change in geometry is typically due to a force acting on the sensor. This force may for example be provided by pressure (e.g. from audio as in a microphone), force, displacement, strain, temperature, acceleration, velocity, rotation, torque, fluid flow, and the like. Thus, when referring to a force sensing system it includes a system for sensing any of the above-mentioned sources of force.

While two sensors, e.g. an accelerometer and a strain sensor, might be based on the same fundamental sensing principle (e.g. piezoresistive or capacitive sensing), it is common to consider such sensors as distinct sensor types. This is primarily due to the differences in actual implementation of the different sensor types (e.g. the use of a proof-mass or not). Thus the present invention includes and applies to all sensors based on this concept of effective index modulation due to a change in geometry of the waveguide and is thereby not limited by the cause of the geometry change and thus includes any sensor type for which a certain measurable quantity can be related to a change in waveguide core geometry and thereby an effective index modulation.

When considering geometry changes in the waveguide core, the term geometry change includes both a change in shape (e.g. from circular to rectangular) and scaling of a geometry (e.g. increasing the size of a rectangular geometry to e.g. twice its initial size).

The present waveguides and optical sensors may be fabricated using MEMS technology. When dealing with optical propagation the most straightforward material to use is silicon. However, the present waveguides and optical sensors may also at least partly be fabricated in metals, polymers, ceramics or any combination thereof, also including silicon.

DESCRIPTION OF DRAWINGS

The invention will now be described in further detail with reference to the drawings in which FIG. 1a illustrates the principle of a Fiber Bragg Grating (FBG), FIG. 1b is a perspective illustration of an optical sensor waveguide according to the invention with a slab-like waveguide, FIG. 1c illustrates the principle of a Bragg grating in a hollow waveguide, FIG. 1d shows the shift in Bragg wavelength as a result of the change in dimension of the waveguide core in FIG. 1b, FIG. 13 shows cross-sectional exemplary illustrations of waveguides with circular confinement of the light and one or more Bragg gratings, FIG. 18 is a perspective illustration of a waveguide chip where the coupling to the core is provided by means of index guided solid core waveguides.

DETAILED DESCRIPTION OF THE INVENTION

Figure 2:
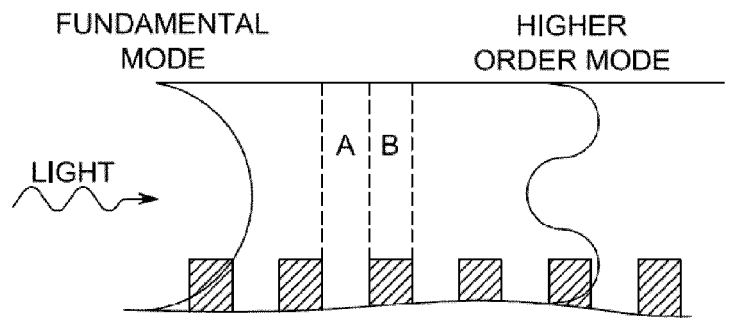
FIG. 2 illustrates examples of spatial confinement of the fundamental mode and a higher order mode propagating in a waveguide incorporating a Bragg grating.

The sensing method of all-optical sensors can in general be divided into amplitude modulated (AM) and frequency modulated (FM) sensing. Frequency modulation refers to the fact that changes in wavelength of the reflected light are used for determining the physical quantity measured, rather than the amplitude of the reflected light as in amplitude modulation. While AM based sensors can achieve extremely high sensitivities due to the on/off characteristics of the signal, the signal is inherently very vulnerable to transmission loss and noise and they are not easily integrated into larger sensor arrays since each sensor requires its own transmission line. On the other hand, FM based sensors do not have nearly the same sensitivity as AM based sensors, however, they are much more robust with respect to noise and are easily integrated into large distributed sensor systems as multiple sensors can share one transmission line.

In most optical waveguides the light is confined inside a core with higher refractive index than the surrounding medium, called the cladding. This method of confining light is denoted total internal reflection. If the core has lower refractive index than the cladding, as for instance a hollow core waveguide, the waveguide is called a "leaky" waveguide.

As stated above a first aspect of the invention is directed to an optical sensor for a force sensing system, comprising a waveguide accommodating a non-solid core for confining light, at least one distributed Bragg reflector, and at least one deflecting element adapted for changing the geometry and/or dimension of the waveguide when submitted to a force. As examples of simple designs the waveguide may be having a solely planar geometry or a solely strip geometry. Further embodiments of the optical sensor according to the invention may be provided with rib or multi-rib geometry waveguides. Naturally the waveguide is suitable and/or adapted for guiding at least one higher order mode of light. Thus, the waveguide may be a multimode waveguide, where the fundamental mode of the light is guided along with a plurality of the higher order mode. The reflected spectrum from the optical sensor will thus contain a plurality of peaks, each peak typically representing a mode. The sensor signal can be inferred from the wavelength shift of one or multiple reflection peaks, or the entire reflection signal (i.e. the spectral fingerprint).

As stated previously a wavelength shift in the reflected Bragg wavelength can not only be obtained by changing the period of the grating, but also by changing the effective refractive index. This could for example be accomplished by altering the dimensions of the waveguide itself. The present optical sensor is preferably based on sensing a change in effective refractive index, rather than a change in Bragg period which is used in conventional FBG sensors, for modulating the Bragg wavelength. The effective index is modulated by modulating the waveguide dimension and/or geometry. Consider two regions, one with only core material and one with both core and grating material. In the region with only core material, the effective index is modulated simply by changing the waveguide dimensions. Low spatial confinement (equivalent to a large core) of the light will increase the effective index while high spatial confinement (equivalent to a small core) will decrease the effective index. In regions with both core and grating material two effects come into play; as before, the index will change in the core part due to higher or lower spatial confinement, but the effective index of the entire region will also depend on how large a fraction of the waveguide mode that is in the grating part of the region and how large a part that is in the core part. If the entire waveguide mode is in the core part, the situation is equivalent to the first case where there is no grating material. But if the mode overlaps an increasing part of the grating the effective index of the entire region will tend towards the effective index of the grating part. The effective index modulation can be along one or multiple axis.

Obviously, the change of the waveguide dimensions is limited by the compliance of the waveguide material. The highest possible compliance is obtained using a hollow core waveguide. Thus, in one embodiment of the invention the non-solid core is hollow. Several hollow core waveguide designs are known in the art, including photonic crystal, distributed Bragg grating and anti-resonance reflecting optical waveguides (ARROWs).

A hollow core waveguide is easy to expand/compress as the compliance of the core is much higher than if the core is filled with a liquid or solid. A high compliance means high sensitivity to physical deformation forces. A solid core is simpler than a typical hollow core when it comes to fabrication and operation, as it can utilize total internal reflection for confining light. This is typically not possible for hollow core waveguides as the refractive index of gasses (e.g. air) is relatively low. Liquid core waveguides can have a higher or lower compliance than solid core waveguides and can utilize total internal reflection for confining light. Liquid core waveguides are beneficial if a substance, e.g. particles or DNA, is to be transported along the core. Examples of methods for confining light in a waveguide other than total internal reflection include photonic crystals, ARROWS, slot waveguides, metallic waveguides, distributed Bragg reflector waveguides and plasmon waveguides.

The waveguide can be e.g. a slab waveguide, a strip waveguide (such as a rectangular waveguide, a circular or half-circular waveguide) or a rib or multi-rib waveguide. The cross-section of the non-solid core may rectangular, polygonal or circular, half-circular, elliptical, half-elliptical or any combination thereof. Similarly the confinement of the core may be substantially rectangular, polygonal or circular, half-circular, elliptical, half-elliptical or any combination thereof.

The slab waveguide is simple to implement, but will only confine light in one direction, hence propagation and coupling losses (especially for the transmitted signal) could be large. Strip and rib waveguides confine light in two directions and will allow for lower coupling losses as light can be guided to a specific in/out-coupling point. This will be essential for multiplexing capabilities, where coupling losses should be minimized. Since a rib waveguide can be considered a combination of a slab and a rectangular waveguide, a high effective index modulation can be achieved as the mode is squeezed from the slab/rectangular part of the waveguide to the rectangular/slab part of the waveguide. This is due to the large difference in confinement (1 or 2 dimensional) between the two situations. Hence a larger effective index modulation is obtainable in e.g. rib waveguide geometries than in simple slab waveguide geometries.

In one embodiment of the invention the maximum width of the waveguide is at least 10 times the maximum height of the waveguide, or at least 20 times, or at least 30 times, or at least 40 times, or at least 50 times, or at least 60 times, or at least 70 times, or at least 80 times, or at least 90 times, or at least 100 times, or at least 500 times, or at least 1000 times, or at least 1500 times, or at least 2000 times, or at least 2500 times, or at least 3000 times, or at least 5000 times, or at least 10000 times, the maximum height of the waveguide.

In one embodiment of the invention the waveguide is an anti-resonance reflecting optical (ARROW) waveguide.

The waveguide may be manufactured from two bonded substrates, such as silicon or pyrex or silica or fused silica substrates. Further, the waveguide may be formed as a recess in a silicon substrate, such as a silicon or pyrex or silica or fused silica substrate. The substrates may be bonded by e.g. welding such as laser welding, gluing, fusion bonding, anodic bonding or eutectic bonding.

Deflecting Element

The sensing capabilities of the optical sensor rely on one or more deflecting elements adapted for changing the geometry and/or dimension of the waveguide when submitted to a force. The waveguide dimensions can be modulated e.g. by using a deflecting beam, membrane, plate or other deflecting mechanical element that either causes a change in the geometry of the waveguide core or modifies the material distribution around the core. It can also be induced directly by compressing/expanding the core. The deflecting element may be a cantilever, a beam, a membrane or plate or similar deflectable construction. The shape of deflecting element can be circular, elliptical, polygonial or a combination. In one embodiment of the invention the deflecting element forms one side of the non-solid core and/or one side of the waveguide.

A deflecting element formed as a thin plate with a uniform thickness will typically deflect with the center of the plate having the largest deflection. Therefore, in a further embodiment of the invention the thickness of the deflecting element is not constant. E.g. the thickness of the deflecting element is varying across the length and/or width of the deflecting element. E.g. said deflecting element may comprise one or more corrugations, e.g. in order to obtain a more uniform deflection at the grating location.

As the deflecting element deflects, the stiffness of the core material (e.g. air) might increase the overall effective stiffness and thus the force required to deflect the deflecting element. To reduce this increased overall effective stiffness, venting holes or back chambers can be introduced in the deflecting element or other part of the waveguide, thereby enabling the waveguide core material (e.g. air) to escape the waveguide core during deflecting element deflection.

In a further embodiment of the deflecting element is suspended by means of one or more beams, such as one or more beams extending across or along the core and/or the waveguide. In a further embodiment the deflecting element forms a hinged element.

In order to prevent mechanical failure of the optical sensor due to a large deflection of the deflecting element, a deflection limiter can be integrated into the present optical sensor. This could be a solid structure situated below the deflecting element, e.g. in the form of a membrane, that prevents the membrane from deflecting more than a certain distance by physical contact. In order to avoid bonding, and thereby e.g. hysteresis, between the deflecting element and the deflection limiter the contact area should be small. This can be achieved by e.g. using pillars as deflection limiters, potentially with a pointed end. The surface material of the limiter could also be chosen to reduce bonding to the material of the deflecting element.

The optical sensor and the deflecting element may be adapted such that the optical sensor is sensitive to a force submitted on top of the deflecting element, thereby resulting in a deflection of the deflecting element which changes the dimension and/or geometry of the waveguide. However, the optical sensor and the deflecting element may also be adapted such that the optical sensor is sensitive to a force submitted from the side of the deflecting element. This may result in a deflection of the deflecting element and/or a displacement of the deflecting element which changes the dimension and/or geometry of the waveguide.

Design of Distributed Bragg Reflector

In one embodiment of the invention said at least one distributed Bragg reflector is a grating. The height of the Bragg reflector (grating) affects the sensitivity of the optical sensor. This is related to the effective index modulation which is partly due to changes in the mode/grating overlap. If the grating height is equal to or larger than the core height, there will be no change in the mode/grating overlap in the core as the core dimensions are modulated (the mode always overlaps the grating completely). Thus the effective index modulation due to change in mode overlap is neglectable. If the grating height is smaller than the full core height the effective index modulation due to core dimension modulation is no longer neglectable.

A given grating height will affect the different waveguide modes differently. This is due to the different spatial distributions of the waveguide modes. Thus, in one embodiment of the invention the maximum height of the distributed Bragg reflector is less than 50% of the maximum height of the waveguide, or less than 40%, or less than 30% or less than 25%, or less than 20%, or less than 15%, or less than 10%, or less than 5% of the maximum height of the waveguide.

If spatial confinement in the waveguide is increased (e.g. due to smaller waveguide dimensions), the effective index of an only-core region will decrease. However, in regions with both core material and grating material (where mode/grating overlap is relevant), the effective index might increase if the refractive index of the grating is larger than the refractive index of the core. This will happen when the decrease in effective index in the core region is smaller than the increase in effective index due to larger overlap between the mode and the high refractive index grating. In determining the optimum grating height the actual modes used for sensing should thus be taken into account. Since very high gratings will cause the reflection peak bandwidth to increase, and at the same time limit the motion of the deflecting element, typical grating heights are in the range 0-25% of the full waveguide height.

In one embodiment of the invention the least one distributed Bragg reflector is formed as a plurality of structures on a surface of the waveguide. These structures may be protrusions or recesses or a combination of both. The shape, height and period of the distributed Bragg Reflector might not be constant along the grating. Varying the height and shape of individual grating elements as well as the period can be used for creating specific reflection spectra. For low index modulations it is well known that the reflection spectrum is related to the spatial distribution of the grating refractive index by a Fourier transform (and the inverse Fourier transform). Thus, in one embodiment of the invention the height and/or width of said structures are varying periodically. Further, the distance between said structures may be varying periodically. Furthermore, the structures may be straight or curved, such as sinusoidal curved or curved as an arc or curved as a parabola. One design could use an apodized Bragg reflector in order to e.g. suppress side lobes. Another possibility is to use a chirped Bragg reflector.

In one embodiment of the invention the optical sensor comprises two or more distributed Bragg reflectors. These distributed Bragg reflectors may be identical or different. An optical sensor comprising two different Bragg reflectors may be utilized for sensing of different "events" as the reflections from each Bragg reflector typically will be distinguishable.

There are numerous possibilities for placing the Bragg reflector(s) in the waveguide. The distributed Bragg reflector can e.g. be located on the deflecting element. Another possibility is that the distributed Bragg reflector is located on a surface of the waveguide opposite the deflecting element.

Coupling

In one embodiment of the invention the optical sensor further comprises a coupling element for coupling light into and/or out of the waveguide. Optimization of the coupling is important for minimizing the coupling loss. The power loss in the coupling of light into the waveguide can be reduced by improving the mode overlap between the fiber mode and the waveguide modes. However, with a multimode waveguide the coupling between an external light source and the waveguide may be even more important. E.g. the amplitude of higher order mode Bragg reflection peaks can be increased by adjusting the angle between a light input in the form of an optical fiber and the waveguide and the positioning of the fiber to the waveguide. This can be an advantage as it makes it easier to measure the signal for higher order modes. At zero angle (i.e. the fiber is parallel to the waveguide) the fundamental mode will typically have the highest amplitude. As the angle is changed from zero, the amplitude of the second order mode will be increased, while the first order mode will decrease in amplitude. At even greater angles the amplitude of even higher order modes will increase and at the cost of the amplitude of lower order modes. Similarly the positioning of the optical fiber with respect to the waveguide will change the amplitude of the individual peaks, as well as the number of peaks. If the optical fiber is aligned to the center of the waveguide, the fundamental mode will typically have the largest amplitude. At off-axis positions higher order mode amplitudes will increase. Thus, in one embodiment of the invention the coupling element is adapted such that light is coupled into the waveguide on-axis/symmetrical with respect to the core. In a further embodiment the coupling element is adapted such that light is coupled into the waveguide off-axis/asymmetrical with respect to the core. Further, the coupling element may be adapted such that light is coupled into the waveguide at a non-zero angle with respect to the core.

Typically the dimension of the waveguide is modulated at the Bragg grating location. Thus, a lead-in coupling directly to this region would cause variations in the coupling loss. A lead-in waveguide section with non-varying dimensions could therefore be positioned in front of the actual sensing location. Also a tapering section or a similar coupling structure between the waveguide and the optical fiber could be used for increasing mode overlap and reducing coupling loss. A coupling structure may be provided by having one or more solid core structures as part of the optical sensor, e.g. as part of a waveguide chip. E.g. the hollow core waveguide may be integrated in a chip and one or more solid core structures provide the optical connection in and/or out of the hollow core waveguide. This solid core structure may be tapered, such that the dimension at one end is adapted to an optical fiber and at the other end adapted to the hollow core. Further, the optical transmission in the solid core structure may be index guided or by means of a photonic crystal or the like.

Examples are illustrated in FIGS. 17a, 17b and 18. In FIGS. 17a and 17b solid core waveguides are provided at each side of the hollow (air) core waveguide. The deflecting element in the form of a membrane is attached to the solid core structures. The waveguide sensor chip in FIG. 18 comprises a hollow core waveguide with a circular deflecting element in the form of a membrane and Bragg grating in the hollow core beneath the membrane. Light is coupled into and out of the hollow core waveguide via two solid core structures in the form of two index guided waveguides on each side of the hollow core. Thus, the solid core waveguides are adapted to function as coupling elements for coupling light into and/or out of the non-solid core of the non-solid core waveguide. The index guided waveguides are funnel shaped at each end to provide tapering towards the output coupling to e.g. an optical fiber but also a tapering towards the hollow core. Light is confined in these solid core index guided waveguides vertically by having a light guiding horizontal layer in the chip surrounded by cladding layers, the light guiding layer having a higher refractive index that the cladding layers, and horizontally by having four recessions/holes in the chip as seen in FIG. 18, where the lower refractive index of the air in the recessions/holes provide for confinement of the light in the cores of the solid core index guided waveguides. The shape of these recessions/holes forms the tapering sections of the solid core index guide waveguide sections. The sensor chip illustrated in FIG. 18 may provide for a low loss coupling to optical fibers at each side of the chip, because the solid core of the optical fiber can be coupled to the solid core structures at the ends of the sensor chip.

The optical sensor may be adapted for propagating light with a wavelength around the telecom spectrum of 1550 nm, e.g. from 1500 to 1620 nm, thereby making it possible to use standard low loss and low cost telecom optical components. In order to take advantage of low-cost interrogation monitor systems the optical sensor may in a further embodiment be adapted for propagating light with a wavelength of approximately 850 nm.

Sensor System

As stated above a further embodiment of the invention is directed to a sensor system comprising at least one light source, one or more optical sensors comprising a sensor optical waveguide accommodating a distributed Bragg reflector, said sensor optical waveguide adapted for guiding at least one higher order mode of the light from said at least one light source, e.g. a multimode optical waveguide, at least one transmitting optical waveguide for guiding light from said at least one light source to said one or more sensor optical waveguides, a detector for measuring light reflected from said Bragg reflector in said one or more sensor optical waveguides, and a data processor adapted for analysing variations in the Bragg wavelength of said at least one higher order mode of the reflected light.

In one embodiment of the invention the sensor system further comprises one or more coupling elements for coupling the light from said at least one transmitting optical waveguide into said one or more sensor optical waveguides. The data processor may be adapted for frequency modulation of the reflected signal. The light source may be a broadband light source and/or a multimode light source. Further, as the data processor is adapted for analysing variations in the Bragg wavelength of said at least one higher order mode of the reflected light it is implicit that the light source is preferably adapted to emit light comprising multiple modes, such as a multimode light source, such as light comprising the first mode, i.e. the fundamental mode, the second mode, the third mode, the fourth mode, the fifth mode, etc. In a leaky mode optical waveguide the loss increases with the mode number.

The sensor system according to the invention may comprise a plurality of multiplexed optical sensors. These optical several sensors can be multiplexed either in a serial, parallel or serial/parallel configuration. The connection between each sensor can be through either optical fiber or on-chip waveguides. Thus several sensor elements with e.g. different Bragg grating design and/or deflecting element design and potentially of different type (temperature, force, acceleration) can be implemented on a single chip with waveguide interconnects. E.g. the distributed Bragg reflector in each optical sensor can be adapted for reflecting a specific and unique wavelength of light as in wavelength division multiplexing. Time multiplexing of the reflected signal may also be employed thereby avoiding the need for a unique reflection from each sensor. Several sensors on one chip will allow for chips with features such as beam forming capabilities (by combining several pressure sensors) and temperature compensation (by combining e.g. a pressure sensor and a temperature sensor). By combining sensors that are affected differently by a given physical quantity (e.g. force) and temperature, temperature compensation can be achieved by e.g. a differential measurement of the reflection signal of the sensors.

In one embodiment of the invention said at least one transmitting optical waveguide is an optical fiber. It may be an advantage to be able to control the polarization of the light, in a further embodiment of the invention the at least one transmitting optical waveguide is a polarization maintaining optical fiber, such as a Panda type PM fiber. The reflected signal will typically propagate back through the same optical fiber that is carrying the light source. Thus, a circulator may be provided to couple the reflected light into the detector.

As stated previously said one or more sensor optical waveguides may be multimode waveguides suitable for guiding a plurality of modes of the light, including the fundamental mode. Thus, consequently the data processor may be adapted for analysing variations in the Bragg wavelength of a plurality of modes of the reflected light, including the fundamental mode.

A spectrometer may be used to analyse the reflected signal from the sensor system such that the reflected signal can be spectrally resolved. However, a more cost-effective solution may be to apply a ratiometric analysis, e.g. by having two or more filters, e.g. band-edge filters, notch filters, band-pass filters, etc., sending the reflected signal through these filters and analysing the ratio between the output from the filters. When the refractive index of the sensor optical waveguide is modulated it will consequently modulate this filter output ratio if the filters are suitably adapted to the wavelength(s) of the light source and the Bragg wavelength(s) of the sensor optical waveguides. One or more simple photo diodes may be employed as a detector and used to monitor this filter output ratio thereby avoiding the use of a possibly expensive spectrometer.

DETAILED DESCRIPTION OF THE DRAWINGS

FIG. 1a illustrates the principle of a FBG with broadband light propagating through the core of the fiber from left to right. A distributed Bragg reflector in the form of a grating with a constant period $\Lambda$ is made by periodically changing the refractive index of a waveguide core, in this case the fiber core. In FIG. 1c the principle is illustrated in a hollow core waveguide. The variation in refractive index acts as a mirror which is selective to a specific wavelength. At each shift in refractive index a reflection of the forward propagating wave will occur. Thus, for specific wavelengths the reflections will add up constructively as each reflection is in phase with the next one thereby providing a peak in the reflected spectrum at the Bragg wavelength $\lambda_B$ according to $$\lambda_B = 2n_{eff}\Lambda$$

where $n_{eff}$ is the average refractive index and $\Lambda$ is the grating period. If the fiber in FIG. 1a is stretched and the period $\Lambda$ of the Bragg grating is changed the Bragg wavelength will change. The simple formula also shows that the Bragg wavelength can be changed by varying the effective index $n_{eff}$ of a waveguide as illustrated in FIGS. 1c and 1d. FIG. 1d shows how a signal may change when the reflected light changes (dashed line to solid line). The change in reflected wavelength can be seen as well.

FIG. 1b is a perspective illustration of an exemplary embodiment of an optical sensor waveguide according to the invention. This strip waveguide is formed as a recess in a substrate and incorporating a distributed Bragg reflector. The deflecting element is formed by another substrate lying on top of the recess thereby forming one side of the waveguide. When a force is submitted on top of the deflecting element it will deflect and thereby change the dimension of the waveguide and thereby change the effective index of the waveguide as the effective index $n_{eff}$ is determined by $$n_{eff} = n_c \sqrt{1 - \left(\frac{m\lambda_B}{2n_c d_c}\right)^2}$$

Where $n_c$ is the core refractive index and $d_c$ is the core height and m is the mode number.

FIG. 2 illustrates the basic principle of optical sensor multimode waveguide. The illustration shows a cross-section of the core with the light propagating from the left. The spatial confinement of the fundamental and a higher order mode is also illustrated. The protrusions at the bottom are the Bragg grating. There are different regions in the waveguide shifting between regions with only core material (illustrated as A) and regions with both core and grating material (illustrated as B). The change in spatial confinement of the mode between regions A and B, changes the effective index of the waveguide. The change in mode-grating overlap changes the geometrically averaged index which varies with the mode order.

Figure 3A:
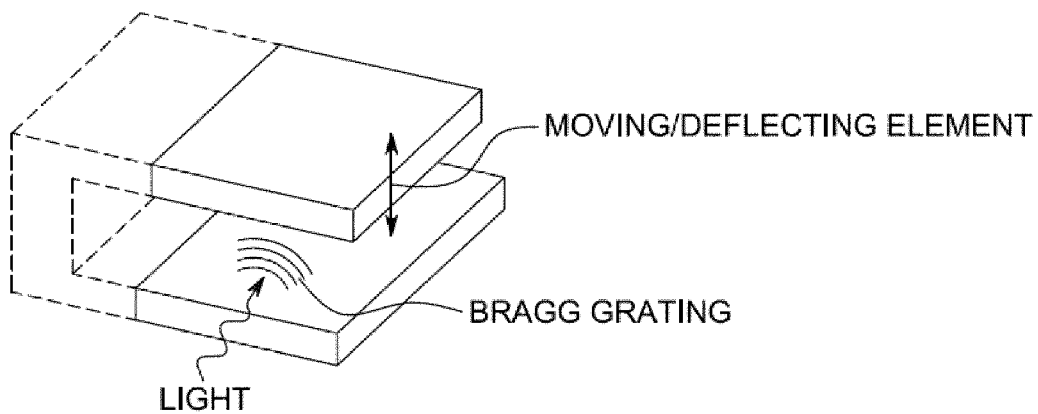
FIG. 3a shows a perspective of a simple slab waveguide with a grating and a deflecting element in the form of a cantilever.

FIG. 3a shows a simple slap waveguide formed between two plates wherein the grating is located on one plate and the other plate is the deflecting element. The two plates can be mechanically connected or not as indicated by the dashed line. When the two plates are connected the deflecting element forms a cantilever.

Figure 3B:
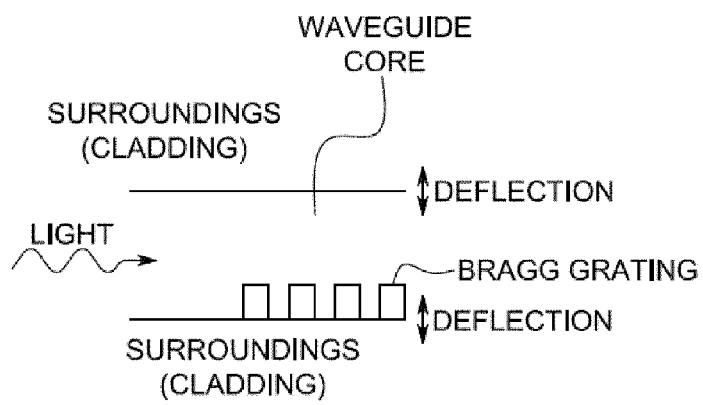
FIG. 3b shows a cross-sectional view of the waveguide from FIG. 3a, FIG. 4 shows an example of the reflection spectrum of a multimode optical sensor waveguide.

FIG. 3b shows the light propagating in core of a waveguide formed between the surrounding cladding layers.

Figure 4:
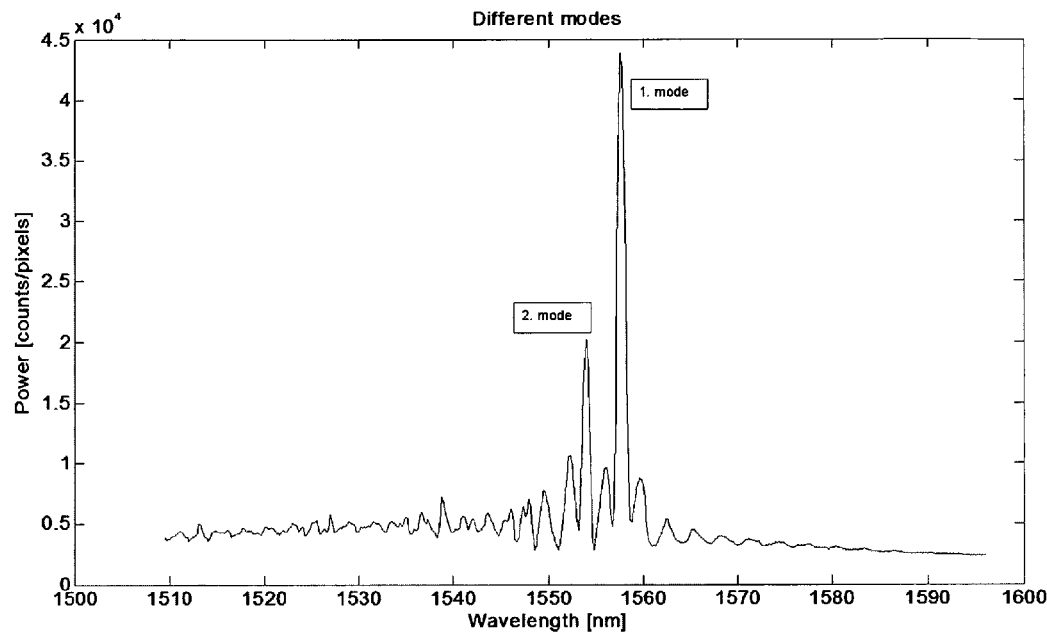

FIG. 4 shows an example of the reflected spectrum from a multimode optical sensor waveguide. Peaks from at least two modes are easily identifiable (fundamental (1.) mode and a higher order (2.) mode). Each mode propagating in the waveguide will typically provide a peak in the reflected spectrum. However, additional peaks may appear in the reflected spectrum as a result of mixing between different modes. The data processor in the present optical sensor is preferably adapted to analyse variations in the peaks from each mode. As previously stated the higher order modes are more sensitive to variations in the refractive index of the waveguide. By adapting the data processor to include analysis of higher order modes the sensitivity of the sensor system can thereby be improved.

Figure 5:
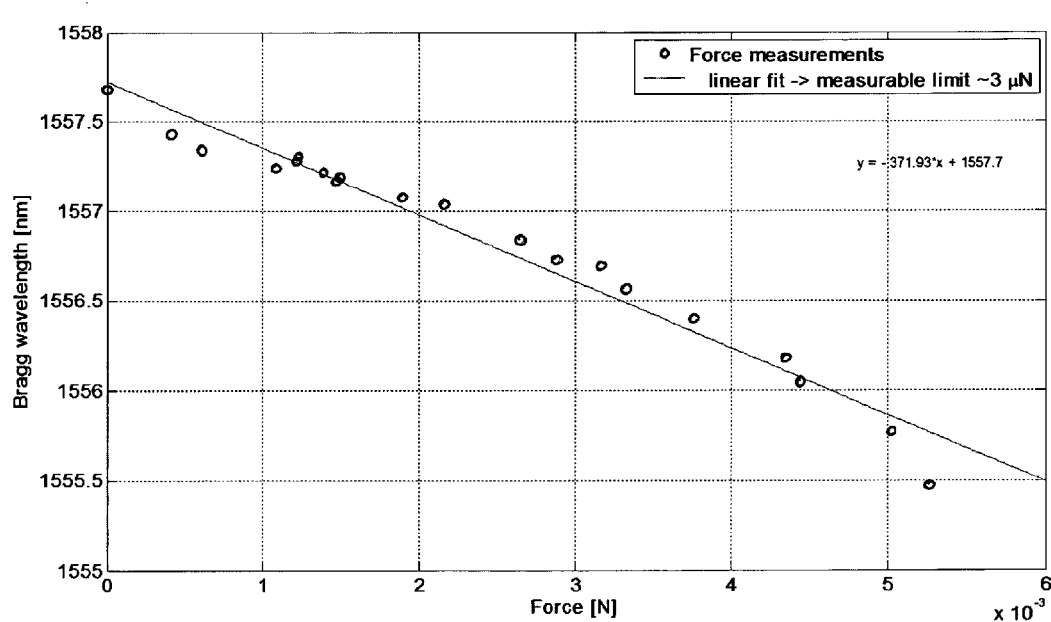
FIG. 5 shows the relation between force and Bragg wavelength displacement.

FIG. 5 shows the relation between a force submitted to an optical sensor according to the invention and the resulting change in Bragg wavelength of the peak in the reflected spectrum. A linear fit has been inserted, all though the change in Bragg wavelength is not in general linear.

There are many ways to design an optical sensor waveguide, e.g. in terms of geometry of waveguide and core, and design, type, location and number of gratings deflecting elements. In the following a number of designs will be proposed.

Figure 6A:
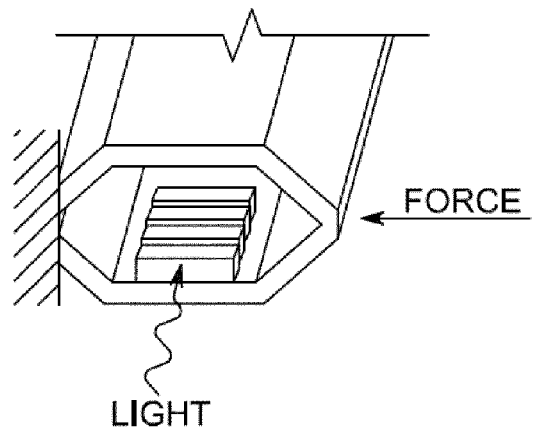
FIGS. 6 & 7 show exemplary design principles of optical sensor waveguides.

FIG. 6a shows a perspective illustration of an optical sensor waveguide adapted for bi-axial deformation of core. When the force is incident from the right as the arrow indicates the substantially hexagonal shaped waveguide will change geometry, almost like an accordion.

Figure 6B:
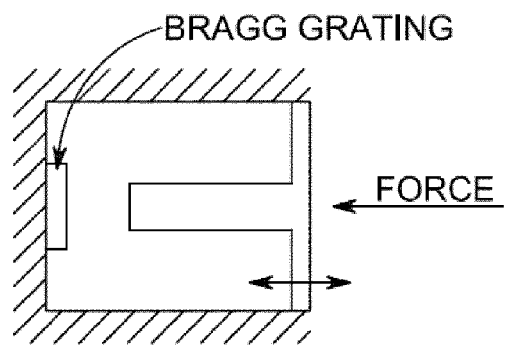

A deflecting element with a piston like structure pointing towards the grating is shown in the cross-sectional illustration in FIG. 6b.

Figure 6C:
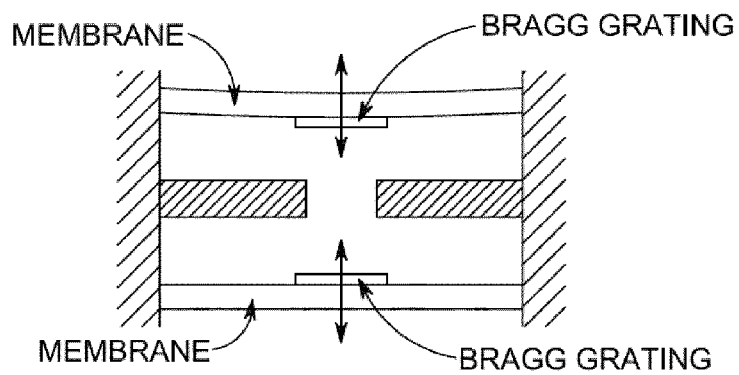

The optical sensor waveguide illustrated in FIG. 6c is provided with two opposing deflecting elements in the form of membranes, each provided with a Bragg grating. The gratings may be different thereby providing different reflection spectra whereby it can be determined which membrane is deflecting. The membranes could have different masses and thereby different resonance/sensitivity.

Figure 7A:
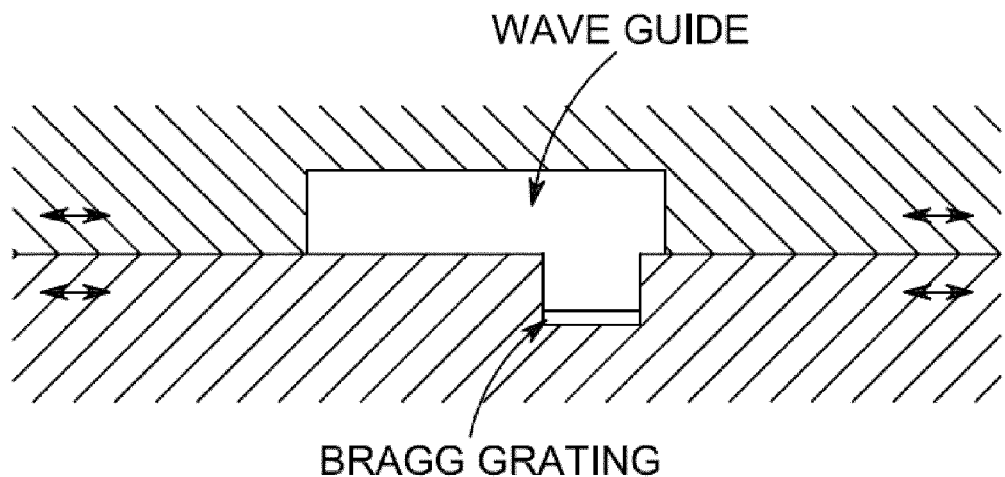

FIG. 7a is a cross-sectional illustration of an asymmetrical waveguide with the core area around the grating. The waveguide is formed from two substrates that are adapted to slide in relation to each other when a force is submitted. This sliding movement will change the geometry of the waveguide and in particular the dimension of the core and thereby the spatial confinement of the light, i.e. the effective refractive index at the grating location changes as the two substrates slide in relation to each other.

Figure 7B:
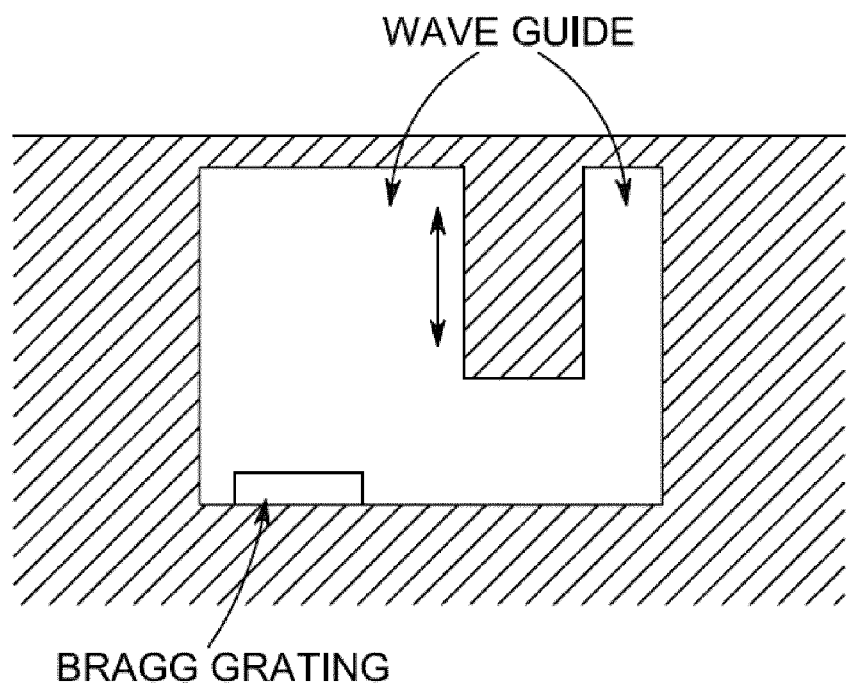

Another cross-sectional illustration of an asymmetrical waveguide is shown in FIG. 7b. This type of design may lead to an increased sensitivity of the corresponding optical sensor waveguide.

The gratings can be designed in many ways to tailor specific needs in terms of wavelength spectrum, sensitivity, etc. Gratings with varying height and spacing are shown in the side view illustrations in FIGS. 8a and 8b, respectively. Grating with different curvatures are shown in the perspective illustrations in FIG. 8c (straight gratings) and 8d (curved gratings).

Figure 9A:
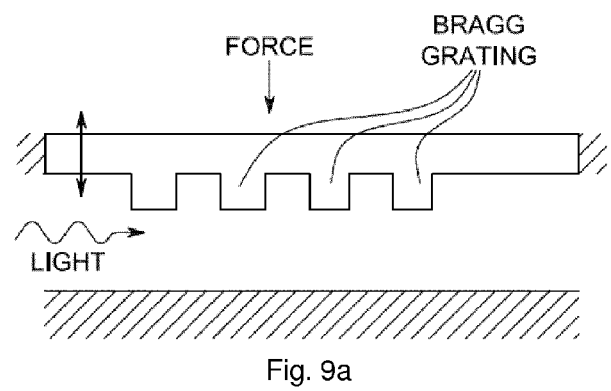
Figure 8D:
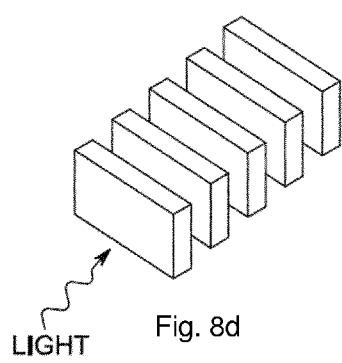
Figure 9B:
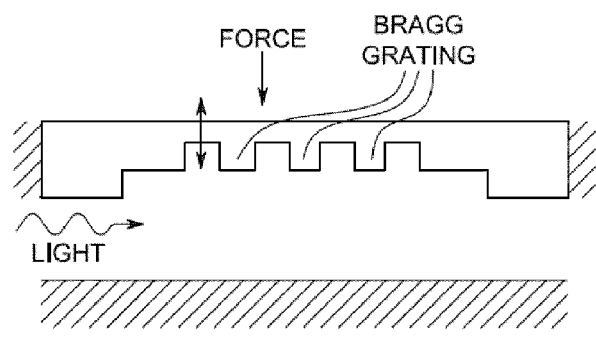

The gratings may be implemented as "normal" gratings formed as protrusions from a surface as illustrated in FIG. 9a or as recesses in a surface as illustrated in FIG. 9b.

Figures 8A, 8B:
FIG. 8 shows different exemplary grating designs, FIG. 9a & b show normal and inverted grating designs, respectively, FIG. 10 show different examples of connecting an optical fiber to a waveguide.
Figure 8C:
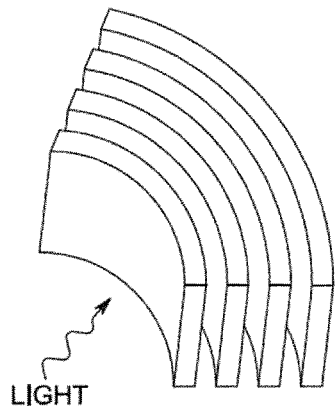

The apodized grating illustrated in FIG. 8a is provided by having a grating with varying height of the protrusions of the grating. However, apodization can also be obtained by arranging the distributed Bragg reflector on a non-plane surface. Examples are illustrated in FIG. 17a and FIG. 17b. In the FIG. 17a the bottom surface of the waveguide hollow core is convex, i.e. curving outwards. The protrusions of the Bragg grating are of equal height but when distributed on the curving bottom the result is a Bragg grating with a height varying along the length of the waveguide core, i.e. in the direction of propagation of the light, whereby the refractive index is varying along the length of the waveguide core. A similar solution is illustrated in FIG. 17b where the bottom surface of the waveguide core is concave, i.e. curving inwards. Again the refractive index of the waveguide is varying along the length of the waveguide core. This effect may be provided when the distributed Bragg reflector is located on a non-plane surface in the direction of propagation of the light.

Figure 10A:
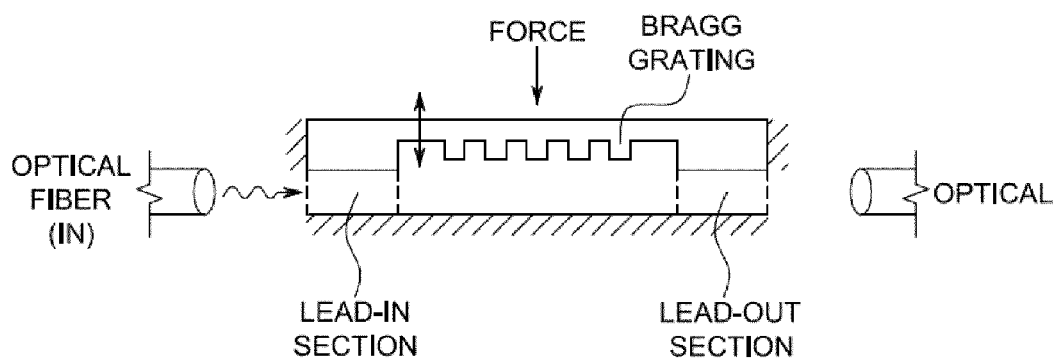
Figure 10B:
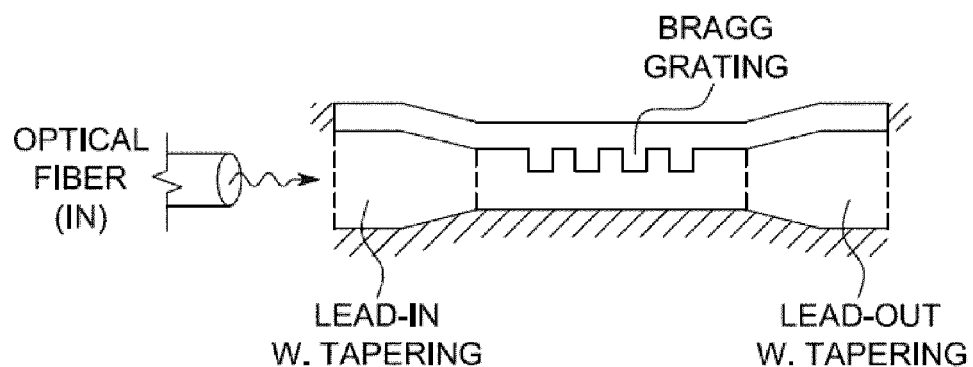

Often an optical fiber must be connected at one or both ends of the waveguide. A straight lead-in/lead-out is illustrated in FIG. 10a whereas a waveguide with tapered sections to improve the coupling efficiency between the fiber and the waveguide is illustrated in FIG. 10b.

Figure 11A:
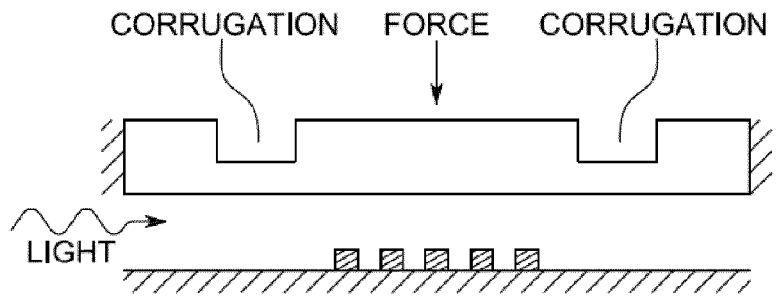
FIG. 11a shows an example of a corrugated deflecting element.

In order to ensure a more uniform deflection of the deflecting element it may be provided with corrugations as illustrated in FIG. 11a.

Figure 11B:
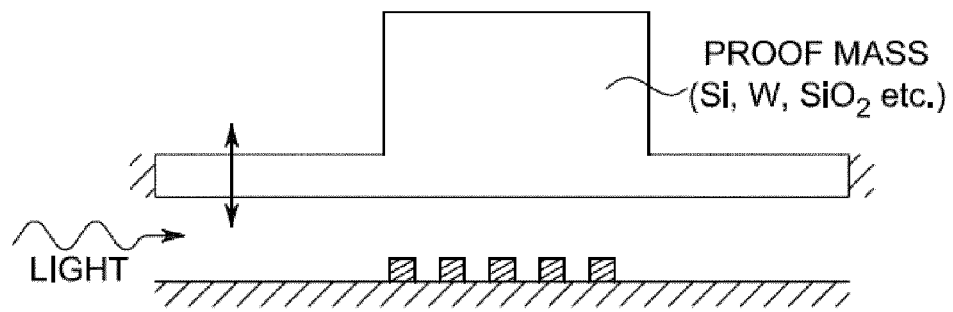
FIG. 11b shows an example of a deflecting element provided with a proof mass to enable detection of acceleration.

The deflecting element may be provided with a local proof mass as illustrated in FIG. 11b to be more sensitive to accelerations of the sensor. Thus, a further embodiment of the invention relates to optical accelerometer comprising a waveguide accommodating a non-solid core for confining light, at least one distributed Bragg reflector, and at least one deflecting element adapted for changing the geometry and/or dimension of the waveguide when submitted to a force, wherein said at least one deflecting element comprises at least one proof mass.

Figure 12:
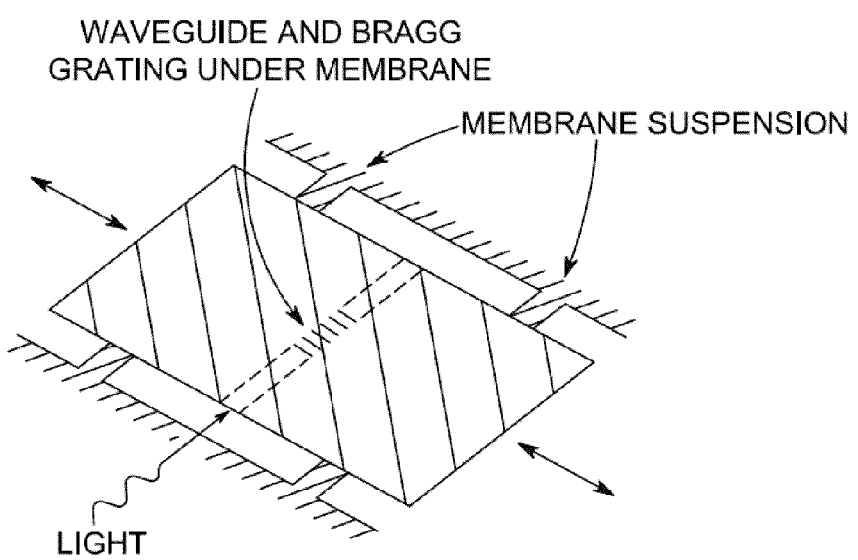
FIG. 12 shows an example of a suspension of the deflecting element using hinges.
Figure 14A:
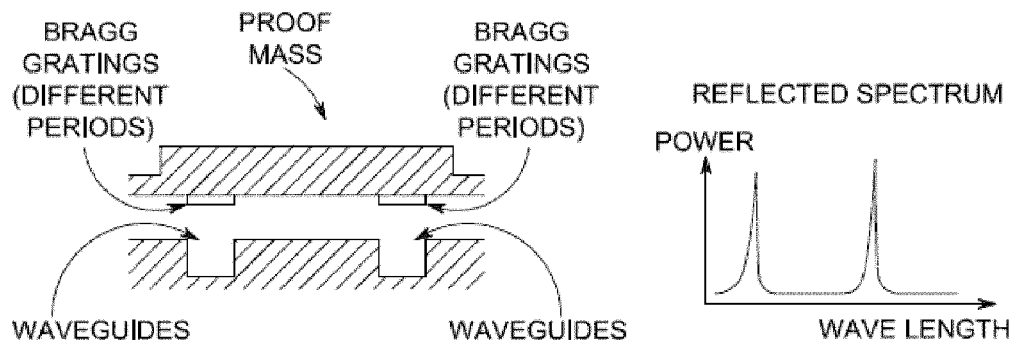
FIG. 14 shows an example of movement detection along two axes for use in e.g. a biaxial accelerometer.
Figure 14B:
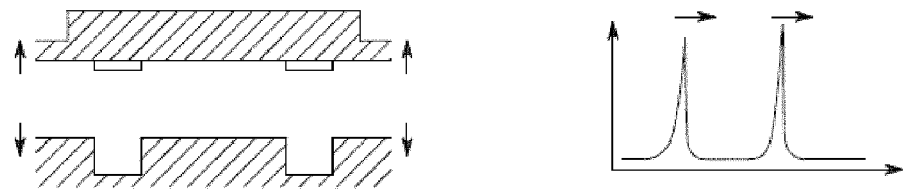
Figure 14C:
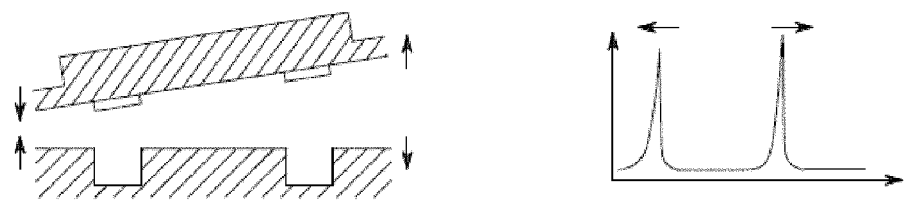
Figure 14D:
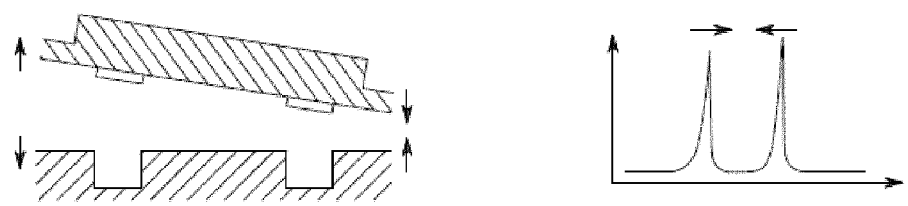

There are different ways of suspending the deflecting element, e.g. depending on the sensor application. In FIG. 12a membrane/plate is elevated over a bottom substrate containing the grating and the waveguide. The membrane/plate is supported only locally by two beams extending parallel to the waveguide. This type of optical sensor is sensitive to movement/deflection of the membrane in both the horizontal and the vertical direction.

A circular shaped waveguide may be provided to reduce the transmission loss. A polarization independent circular confinement is illustrated in FIG. 13a with two opposed gratings. FIG. 13b also has a circular confinement, but with only one grating the propagation is polarization dependent.

FIG. 14 illustrates a principle of a sensor that is sensitive to where the force is submitted. Two waveguides sharing the same deflecting element are provided. Each waveguide is provided with a different Bragg grating, whereby the different waveguides can be distinguished in the reflected spectrum. If the force is submitted on top of the deflecting element such that the deflection in each waveguide is identical, the reflected Bragg peaks will be displaced equally, as shown in the reflected spectrum in FIG. 14b. However if the deflection is asymmetrical it will be seen in the reflected spectrum as illustrated in FIGS. 14c and 14d. Thereby e.g. movement/acceleration will be detectable in two dimensions by comparison of the multiple reflected signals.

Figure 15A:
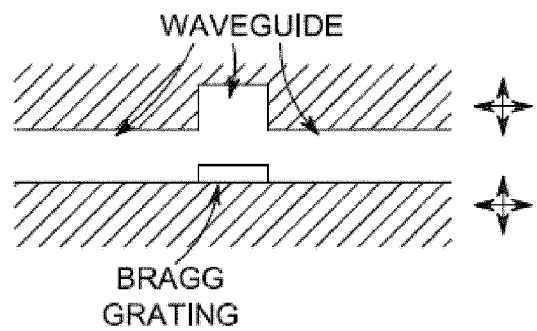
FIG. 15 shows another example of movement detection along two axes, FIG. 16a & b show multiplexing of a plurality of optical sensors, FIG. 17a & b show apodized gratings obtained by means of curved bottom surfaces of the waveguide.
Figure 15B:
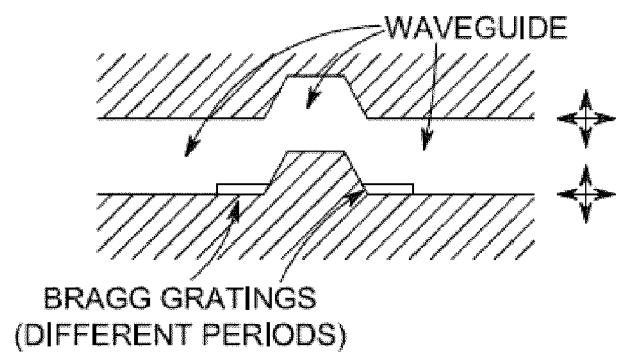
Figure 15C:
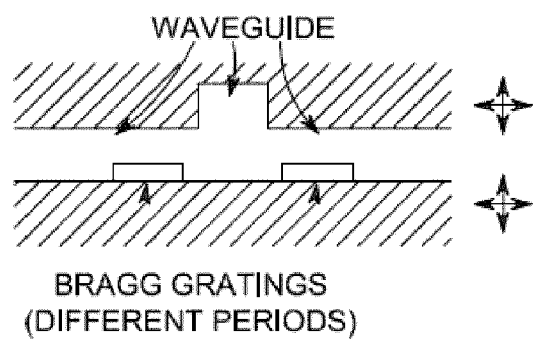

FIG. 15 provides illustrations of other waveguide designs that will be sensible to movement detection in two directions.

Figure 16A:
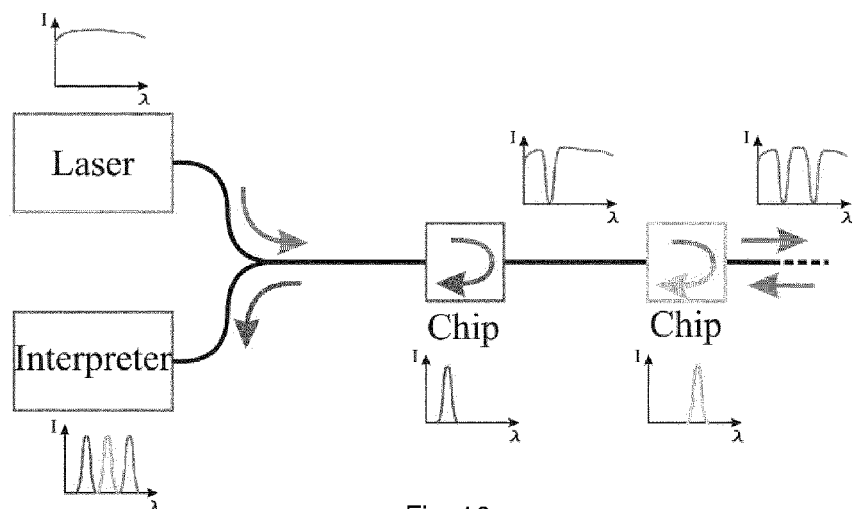
Figure 16B:
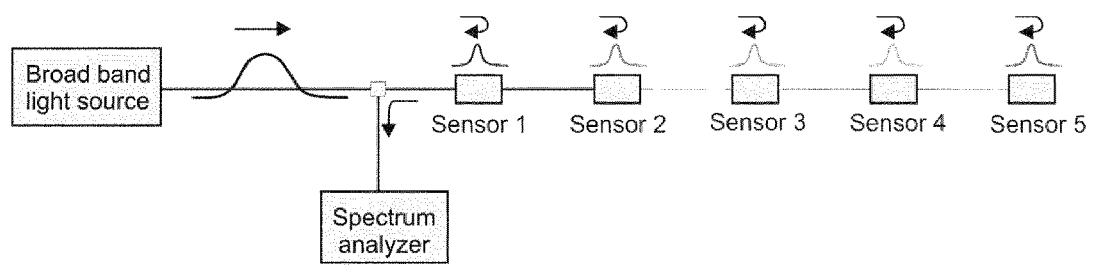

FIG. 16 shows how a plurality of optical sensors can be (frequency) multiplexed along the same transmission line.

FURTHER DETAILS OF THE INVENTION

The invention will now be described in further detail with reference to the following items:
1. An optical sensor for a force sensing system, comprising a waveguide accommodating
   a non-solid core for confining light,
   at least one distributed Bragg reflector, and at least one deflecting element adapted for changing the geometry and/or dimension of the waveguide when submitted to a force.
2. The optical sensor of item 1, wherein the waveguide is having a planar geometry.
3. The optical sensor of item 1, wherein the waveguide is having a strip geometry.
4. The optical sensor of item 1, wherein the waveguide is having a rib geometry.
5. The optical sensor according to any of the preceding items, wherein said non-solid core is hollow.
6. The optical sensor according to any of the preceding items, wherein the cross-section of said non-solid core is rectangular, polygonal or circular or elliptical or any combination thereof.
7. The optical sensor according to any of the preceding items, wherein the confinement of the core is substantially rectangular, polygonal or circular or elliptical.
8. The optical sensor according to any of the preceding items, wherein the waveguide is a multimode waveguide.
9. The optical sensor according to any of the preceding items, wherein said deflecting element forms one side of the non-solid core and/or one side of the waveguide.
10. The optical sensor according to any of the preceding items, comprising two deflecting elements.
11. The optical sensor according to any of the preceding items, wherein said deflecting element is a beam, plate, membrane or cantilever.
12. The optical sensor according to any of the preceding items, wherein said deflecting element comprises one or more corrugations.
13. The optical sensor according to any of the preceding items, wherein said deflecting element comprises venting holes.
14. The optical sensor according to any of the preceding items, further comprising one or more back chambers.
15. The optical sensor according to any of the preceding items, wherein said deflecting element forms a hinged element.
16. The optical sensor according to any of the preceding items, wherein said deflecting element is suspended by means of one or more beams, such as one or more beams extending across or along the core.
17. The optical sensor according to any of the preceding items, wherein the thickness of the deflecting element is varying across the length and/or width of the deflecting element.
18. The optical sensor according to any of the preceding items, wherein said at least one deflecting element comprises at least one proof mass.
19. The optical sensor according to any of the preceding items, further comprising one or more deflection limiters for limiting the deflection of the deflecting element, deflection limiters such as pillars, such as pillars with a pointed end.
20. The optical sensor according to any of the preceding items, wherein the force is submitted on top of the deflecting element.
21. The optical sensor according to any of the preceding items, wherein the force is submitted from the side of the deflecting element.
22. The optical sensor according to any of the preceding items, wherein said at least one distributed Bragg reflector is a grating.
23. The optical sensor according to any of the preceding items, comprising two or more distributed Bragg reflectors.
24. The optical sensor according to item 23, wherein said distributed Bragg reflectors are identical.
25. The optical sensor according to item 23, wherein said distributed Bragg reflectors are different.
26. The optical sensor according to any of the preceding items, wherein the shape of said at least one distributed Bragg reflector is apodized.
27. The optical sensor according to any of the preceding items, wherein said at least one distributed Bragg reflector is located on a non-plane surface, such as a concave or convex surface, such that a varying height, i.e. apodization, of the Bragg reflector is provided.
28. The optical sensor according to any of the preceding items 26 to 27, wherein the apodization is provided in the direction of propagation of light in the non-solid core.
29. The optical sensor according to any of the preceding items, wherein the shape of said at least one distributed Bragg reflector is chirped.
30. The optical sensor according to any of the preceding items, wherein said at least one distributed Bragg reflector is formed as a plurality of structures on a surface of the waveguide.
31. The optical sensor according to item 30, wherein said structures are protrusions or recesses or a combination of both.
32. The optical sensor according to any of the preceding items 30 to 31, wherein the height and/or width of said structures are varying periodically.
33. The optical sensor according to any of the preceding items 30 to 32, wherein the distance between said structures is varying periodically.
34. The optical sensor according to any of the preceding items 30 to 33, wherein the structures are straight or curved, such as sinusoidal curved or curved as an arc or curved as a parabola.
35. The optical sensor according to any of the preceding items, wherein the maximum height of the distributed Bragg reflector is less than 50% of the maximum height of the waveguide, or less than 40%, or less than 30% or less than 25%, or less than 20%, or less than 15%, or less than 10%, or less than 5% of the maximum height of the waveguide.
36. The optical sensor according to any of the preceding items, wherein said at least one distributed Bragg reflector is located on the deflecting element.
37. The optical sensor according to any of the preceding items, wherein said at least one distributed Bragg reflector is located on a surface of the waveguide opposite the deflecting element.
38. The optical sensor according to any of the preceding items, wherein the maximum width of the waveguide is at least 10 times the maximum height of the waveguide, or at least 20 times, or at least 30 times, or at least 40 times, or at least 50 times, or at least 60 times, or at least 70 times, or at least 80 times, or at least 90 times, or at least 100 times the maximum height of the waveguide.
39. The optical sensor according to any of the preceding items, wherein the waveguide is an anti-resonance reflecting optical (ARROW) waveguide.

40. The optical sensor according to any of the preceding items, wherein the waveguide is manufactured from two bonded substrates, such as silicon or pyrex or silica or fused silica substrates.
41. The optical sensor according to any of the preceding items, wherein the waveguide is formed as a recess in a silicon substrate, such as a silicon or pyrex or silica or fused silica substrate.
42. The optical sensor according to any of the preceding items, wherein the waveguide is suitable and/or adapted for guiding at least one higher order mode of light, such as a multimode waveguide.
43. The optical sensor according to any of the preceding items, further comprising one or more, preferably two, solid core waveguides adjacent to the non-solid core waveguide.
44. The optical sensor according to item 43, wherein said one or more solid core waveguides are index guided solid core waveguides.
45. The optical sensor according to item 43, wherein said one more solid core waveguides are photonic crystal or photonic band gap waveguides.
46. The optical sensor according to any of the preceding items 43 to 45, wherein said one or more solid core waveguides are adapted to function as coupling elements for coupling light into and/or out of the non-solid core of the non-solid core waveguide.
47. The optical sensor according to any of the preceding items 43 to 46, wherein the dimension of one end of the solid core of said one or more solid core waveguides is adapted to the dimension of the non-solid core of the non-solid core waveguide.
48. The optical sensor according to any of the preceding items 43 to 47, wherein the dimension of one end of the solid core of said one or more solid core waveguides is adapted to the dimension of a transmission waveguide, such as an optical fiber.
49. The optical sensor according to any of the preceding items 43 to 48, wherein the mode field of one end of the solid core of said one or more solid core waveguides is adapted to the mode field of the non-solid core waveguide.
50. The optical sensor according to any of the preceding items 43 to 49, wherein the mode field of one end of the solid core of said one or more solid core waveguides is adapted to the mode field of a transmission waveguide, such as an optical fiber.
51. The optical sensor according to any of the preceding items 43 to 50, wherein said one or more solid core waveguides are tapered at one or both ends of the waveguides.
52. The optical sensor according to any of the preceding items 43 to 51, wherein the non-solid core waveguide and said one or more solid core waveguides are manufactured from two bonded substrates, such as silicon or pyrex or silica or fused silica substrates.
53. The optical sensor according to any of the preceding items 52, wherein said one or more solid core waveguides are defined vertically by at least three horizontal layers on one of the substrates where the middle layer is having a higher refractive index that the upper and lower cladding layers.
54. The optical sensor according to any of the preceding items 52 to 53, wherein said one or more solid core waveguides are defined horizontally by vertical recessions in or holes through at least one of the substrates.
55. The optical sensor according to any of the preceding items, further comprising a coupling element for coupling light into and/or out of the waveguide.
56. The optical sensor according to item 55, wherein said coupling element is adapted such that light is coupled into the waveguide on-axis/symmetrical with respect to the core.
57. The optical sensor according to item 55, wherein said coupling element is adapted such that light is coupled into the waveguide off-axis/asymmetrical with respect to the core.
58. The optical sensor according to any of items 55 to 57, wherein said coupling element is adapted such that light is coupled into the waveguide at a non-zero angle with respect to the core.
59. The optical sensor according to any of the preceding items, wherein said at least one deflecting element is adapted for changing the geometry and/or dimension of the waveguide when submitted to a force originating from pressure, displacement, strain, temperature, acceleration, velocity, rotation, torque, fluid flow and/or temperature.
60. Use of the optical sensor according to any of items 1 to 59 in a force sensing system.
61. A force sensing system comprising an optical sensor according to any of items 1 to 59.
62. A sensor system comprising
    at least one light source,
    one or more optical sensors comprising a sensor optical waveguide accommodating a distributed Bragg reflector, said sensor optical waveguide adapted for guiding at least one higher order mode of the light from said at least one light source,
    at least one transmitting optical waveguide for guiding light from said at least one light source to said one or more sensor optical waveguides,
    a detector for measuring light reflected from said Bragg reflector in said one or more sensor optical waveguides, and
    a data processor adapted for analysing variations in the Bragg wavelength of said at least one higher order mode of the reflected light.
63. A sensor system comprising
    at least one light source,
    one or more optical sensors comprising a multimode sensor optical waveguide accommodating a distributed Bragg reflector,
    at least one transmitting optical waveguide for guiding light from said at least one light source to said one or more sensor optical waveguides,
    a detector for measuring light reflected from said Bragg reflector in said one or more multimode sensor optical waveguides, and
    a data processor adapted for analysing variations in the Bragg wavelength of at least one higher order mode of the reflected light.
64. The sensor system of any of items 62 to 63, further comprising one or more coupling elements for coupling the light from said at least one transmitting optical waveguide into said one or more sensor optical waveguides.
65. The sensor system of any of items 62 to 64, wherein said data processor is adapted for frequency modulation of the reflected signal.

66. The sensor system of any of items 62 to 65, further comprising a coupling element, such as a circulator, for coupling light reflected from said Bragg reflector into said detector.
67. The sensor system of any of items 62 to 66, wherein the light source is a broadband light source.
68. The sensor system of any of items 62 to 67, wherein the light source is a multimode light source such that the light guided in the sensor optical waveguide, the transmission waveguide and the reflected light is multimode light.
69. The sensor system of any of items 62 to 68, wherein the sensor system comprises a plurality of multiplexed optical sensors.
70. The sensor system of any of items 62 to 69, wherein the sensor system comprises a plurality of multiplexed optical sensors, and wherein the distributed Bragg reflector in each optical sensor is adapted for reflecting a specific and unique wavelength of light.
71. The sensor system of item 70, wherein said plurality of optical sensors are multiplexed in a serial, parallel or serial and parallel configuration.
72. The sensor system of any of items 62 to 71, wherein said one or more optical sensors are suitable for sensing a change in pressure, displacement, strain, temperature, acceleration, velocity, rotation, torque, fluid flow or temperature.
73. The sensor system of any of items 62 to 72, wherein said at least one transmitting optical waveguide is an optical fiber.
74. The sensor system of any of items 62 to 73, wherein said at least one transmitting optical waveguide is a polarization maintaining optical fiber, such as a Panda type PM fiber.
75. The sensor system of any of items 62 to 74, wherein said one or more sensor optical waveguides are furthermore suitable for guiding the fundamental mode of the light and wherein said data processor is adapted for analysing variations in the Bragg wavelength of the fundamental mode of the reflected light.
76. The sensor system of any of items 62 to 75, wherein one or more optical sensors is one or more of the optical sensor according to any of items 1 to 59.
77. A method for improving the sensitivity of a sensor system comprising at least one sensor optical waveguide suitable for guiding at least one higher order mode of light, said method comprising the step of analysing a plurality of reflected signals from the optical sensor system for detecting a change in Bragg wavelengths of said at least one higher order mode of the reflected light.

The invention claimed is:

1. An optical sensor comprising a sensor chip, the sensor chip comprising:
   a hollow core waveguide defining a hollow core and comprising at least one distributed Bragg reflector,
   at least one solid core waveguide adjacent the hollow core waveguide, each waveguide of the at least one solid core waveguide being configured as a respective coupling element to couple light at least one of into and out of the hollow core of the hollow core waveguide, and
   at least one deflecting element configured to change at least one of geometry and dimension of the hollow core waveguide when submitted to a force.

2. The optical sensor according to claim 1, wherein said at least one solid core waveguide has at least one of a slab geometry, a strip geometry and a rib geometry.
3. The optical sensor according to claim 1, wherein said force originates from at least one of pressure, displacement, strain, temperature, acceleration, velocity, rotation, torque, fluid flow and temperature.
4. The optical sensor according to claim 1, wherein two bonded substrates collectively form both said hollow core waveguide and said solid core waveguide.
5. The optical sensor according to claim 4, wherein the two bonded substrates are selected from the group consisting of silicon substrates, silica substrates and fused silica substrates.
6. The optical sensor according to claim 4, wherein said at least one solid core waveguide is defined vertically by at least three horizontal layers on one of the two bonded substrates.
7. The optical sensor according to claim 4, wherein said at least one solid core waveguide is defined horizontally by vertical recessions.
8. The optical sensor according to claim 1, wherein said at least one deflecting element forms one side of the hollow core of the hollow core waveguide.
9. The optical sensor according to claim 1, wherein said deflecting element comprises an item selected from the list consisting of a beam, a plate, a membrane and a cantilever.
10. The optical sensor according to claim 1, wherein said at least one deflecting element comprises at least one proof mass.
11. The optical sensor according to claim 1, wherein said at least one distributed Bragg reflector comprises a grating.
12. The optical sensor according to claim 1, wherein at least one of said at least one distributed Bragg reflector is located opposite the at least one deflecting element.
13. The optical sensor according to claim 1, wherein the hollow core waveguide comprises an anti-resonance reflecting optical (ARROW) waveguide.
14. The optical sensor according to claim 1, wherein said at least one solid core waveguide is selected from the group consisting of index guided solid core waveguides, anti-resonance reflecting optical (ARROW) waveguides, photonic crystal waveguides, and photonic band gap waveguides.
15. The optical sensor according to claim 1, wherein geometry of the hollow core waveguide is selected from the list consisting of planar geometry only, strip geometry only, rib geometry only, and slab geometry only.
16. The optical sensor according to claim 1, wherein each of the at least one hollow core waveguide is configured to guide at least one of a fundamental mode of single mode light and a fundamental mode and at least one higher order mode of multimode light.
17. The optical sensor according to claim 1, wherein the maximum height of the distributed Bragg reflector is less than 25% of the maximum height of the hollow core of the hollow core waveguide.
18. The optical sensor according to claim 1, wherein the maximum width of the hollow core waveguide is at least 10 times larger than the maximum height of the hollow core waveguide.

* * * * *